United States Patent [19]

Roth et al.

[11] 4,199,561

[45] Apr. 22, 1980

[54] COATED NUTRIENTS AND MEDICAMENTS FOR VETERINARY USE

[75] Inventors: Harold H. Roth, Bay City; Peter W. Owen; Thomas T. Chiu, both of Midland, all of Mich.

[73] Assignee: The Dow Chemical Company, Midland, Mich.

[21] Appl. No.: 15,037

[22] Filed: Feb. 26, 1979

[51] Int. Cl.$^2$ .................. A61K 31/74; A61K 9/32
[52] U.S. Cl. ............................ 424/32; 424/19; 424/21; 424/22; 424/81
[58] Field of Search .................. 424/19–22, 424/32, 33, 78, 81

[56] References Cited

U.S. PATENT DOCUMENTS

| | | | |
|---|---|---|---|
| 3,453,360 | 7/1969 | Hill | 424/81 |
| 3,477,995 | 11/1969 | Negoro | 260/73 |
| 3,553,313 | 1/1971 | Tort | 424/32 |
| 3,619,200 | 11/1971 | Ferguson et al. | 99/2 |
| 3,764,477 | 10/1973 | Lehmann et al. | 195/63 |
| 3,766,203 | 10/1973 | Sumida | 260/309.6 |
| 3,803,302 | 4/1974 | Miner et al. | 424/81 |
| 3,829,564 | 8/1974 | Merry et al. | 424/78 |
| 3,919,436 | 11/1975 | Takebe et al. | 427/3 |
| 3,968,277 | 7/1976 | Takase | 427/212 |
| 4,001,389 | 1/1977 | Fildes | 424/32 |

*Primary Examiner*—Shep K. Rose
*Attorney, Agent, or Firm*—M. B. Davey; E. E. Schilling; R. G. Brookens

[57] ABSTRACT

An imidazoline modified styrene-acrylonitrile polymer composition which is substantially insoluble in aqueous media at about pH 6 or more but swellable or soluble at pH 3 or less is employed as a coating for nutrient or therapeutic substances for administration to ruminants. The substances thus are rendered resistant to attack and breakdown in the rumen yet remain susceptible to release and digestion within the abomasum or small intestine of the animal.

14 Claims, No Drawings

COATED NUTRIENTS AND MEDICAMENTS FOR VETERINARY USE

The present invention relates to compositions that are specially useful for preserving and protecting sensitive materials that undergo undesired reaction when they are subjected to degradative environments.

Methods for temporarily protecting reactive materials, such as medicaments, while the medicaments are exposed to environments which ordinarily tend to degrade or decompose the medicament have been known for many years. For example, certain drugs that ordinarily react in an undesirable manner in the acidic environment of the stomach have been coated heretofore with various materials that are resistant to the action of acids. In this manner, drugs for human consumption are sometimes protected during their passage through the stomach. The protective coatings are selected so that, after the passage of the coated material through the stomach, the coating decomposes in the more basic environment of the intestine, thereby releasing the drugs (chemically unchanged) at the place in the body where the drug will be most effectively absorbed. Such coatings have been termed "enteric coatings."

In the case of ruminants such as sheep and cattle, medicaments having "enteric coatings" are, unfortunately, usually not protected from the drastic treatments afforded in the rumens of such animals. Medicaments given orally to ruminants first pass directly into the rumen, which has a large population of microorganisms and is either neutral or slightly acidic. From the rumen the materials then pass into the more acidic abomasum, and subsequently into the animal's intestine. In the case of ruminants, many medicaments, including many desirable nutrients or feedstuffs, such as vitamins, amino acids, and the like, are decomposed or metabolized to at least some extent in an undesirable manner in the environment of the rumen. Such decomposition makes oral treatment of ruminants with such susceptible materials either expensive or impossible.

Thus, there is a definite need, particularly in the fields of veterinary medicine and ruminant nutrition, for a method whereby materials that are ordinarily degraded in the ruminant environment can be administered orally to ruminants without such a high degree of degradation taking place.

SUMMARY OF THE INVENTION

It has now been discovered that materials intended to be administered orally to ruminants can be effectively protected from the ruminant environment if the materials are first coated with a polymer composition of an imidazoline modified styrene-acrylonitrile polymer and preferably an hydroxyethylimidazoline modified styrene-acrylonitrile polymer containing from about 15 to about 35 weight percent polymerized acrylonitrile and, correspondingly from about 85 to about 65 weight percent styrene, and having a molecular weight of from about 60,000 to about 200,000, which polymer contains from 14 to 23 mole percent hydroxyethyl imidazoline modification. It has been found that these polymers resist not only the extremely degradative microbial environment in the rumen, but also the solubilizing action of the rumen in vivo fluid (which has a pH from about 5.5 to about 6.5 or more). The imidazoline modified polymer has been found to remain insoluble at about pH 6 or higher for periods of from about 16 to about 20 hours but is soluble in less than 3 hours at about pH 3 or lower and has therefore been found to be highly suitable in the present invention.

These criteria have been arrived at by consideration of the conditions normally existing in the ruminant digestive system. For normal feedstuffs the residence time in the rumen is from about 4 to about 72 hours, usually around 20 hours, and the residence time in the abomasum and lower intestine is rarely more than 3 hours and frequently less than 30 minutes.

DETAILED DESCRIPTION OF THE INVENTION

The protective medicament and nutrient compositions of this invention can be used successfully when a composition consists mainly of the material to be protected, covered with a very thin continuous layer of the imidazoline modified polymer (wherein the weight of the coating can represent as little as about 5 weight percent or less, but is generally from about 5 weight percent to about 80 weight percent of the total weight of the composition). Preferably, but not necessarily, the medicament or nutrient portion of the rumen stable compositions of this invention should be solid at temperatures below about 40° C. Typical, nonlimiting examples of medicaments that can be utilized in the practice of this invention include anthelmintics such as crufomate, antibiotics such as chloramphenicol, bacitracin, bacitracin zinc, erythromycin, oxytetracycline and the like, antibacterials, antivirals, insecticides, growth stimulants, anthelmintics, hormones, vaccines, estrogens, androgens, steroids, tranquilizers and analgesics as well as materials that are often considered as nutrients of feedstuffs such as carbohydrates, fats, proteins, amino acids, vitamins, minerals and the like. For purposes of the present invention such "nutrients" can be considered the equivalent and inclusive of "medicaments" and "feedstuffs."

In order to obtain coated medicaments in the practice of the present invention, the polymer coating material is dissolved in a selected organic solvent. Suitable solvents include, for example, aliphatic hydrocarbons, such as hexane, cyclohexane or the like; aromatic hydrocarbons, such as toluene and the like; halogenated hydrocarbons, such as trichloroethylene, methylene chloride, chloroform and the like; aliphatic esters, such as ethylacetate or ketones such as acetone and methylethyl ketone, alcohols such as methanol, ethanol and alcohol mixtures and the like, and subsequently spray the resulting solution over particles of the medicament to be protected. Generally, the viscosity of the polymer coating material employed is in the range of from about 10 to about 200 cps.

The particles generally result by simply compressing the material to be protected into a so-called unit dosage form such as a tablet or a smaller particle, several which can be used simultaneously as a unit dose, if desired. Such particles can also be prepared by utilizing known extrusion methods. Conventional methods for coating particulated medicaments and nutrients such as, for example, conventional pill coating procedures, pan coating or fluidized bed procedures can also be readily utilized by those skilled in the art in the preparation of the coated products of the present invention.

In the treatment of ruminants, the rumen stable medicament and/or nutrient compositions of the present invention are generally admixed with the ordinary feed that is to be consumed by the ruminants. Therefore, improved feed compositions comprising a blend of common animal food material with a solid, particulated rumen stable imidazoline polymer coated medicament or nutrient material that can be solubilized in the presence of gastric and/or intestinal fluids constitutes one of the preferred embodiments of the present invention.

It should be understood that the imidazoline polymer composition of this invention need not necessarily be used in the pure state for successful results. For example, other materials (in addition to the medicament and/or nutrient) can also be present in significant amounts in the compositions of this invention, so long as the basic protective abilities of the polymer composition are not destroyed. Materials such as dyes, stabilizers, pigments, plasticizers (such as esters of phthalic acid, e.g., dibutyl-, diethyl-, butylbenzyl- and dioctyl triphenylphosphate-; polyethyleneglycol and the like), can be present in the protected medicaments and/or nutrients of this invention, in some instances, in amounts up to about 10 weight percent, if desired.

The nutrient or therapeutic material may be in the form of discrete bodies or particles or spheres having a substantially continuous surface coating of the polymer or it may be a mixture in which particles of the material are dispersed throughout a matrix of the polymer. Other combinations are also possible, such as an agglomeration of individually surface-coated particles bonded together by the polymer. The coating thickness of polymer on such beads or particles usually ranges from about 20 to about 200 microns.

Where appropriate, the nutrient or therapeutic composition may be in the form of a comparatively large body such as a tablet or lozenge. Generally, however, the composition will be in the form of small sized particles of from about 0.1 to about 2.0 mm., preferably of the order of about 1.0 mm., more preferably between 0.1 and 1.0 mm. Particles of this size can readily pass between the rumen and the abomasum and are not readily trapped by froth in the rumen, thus minimizing losses by mastication. For similar reasons the density of the composition should be as near as practicable to unity. The compositions of the present invention may include two or more nutrients or therapeutic agents and may in addition include biologically inert adjuvants or filler materials to adjust the density or other physical properties of the compositions as discussed above. The present invention also extends to include a method for rendering a nutrient or therapeutic material resistant to microbial attack within the rumen of ruminant animals which method comprises the step of treating the material with the polymer hereinbefore described.

Such a treatment may involve the coating of discrete bodies or particles of the nutrient or therapeutic material with the polymer or the incorporation of such bodies or particles into a matrix of the polymer as hereinbefore described. Another alternative is the precoating of such particles followed or accomplished by agglomeration of the coated particles into larger aggregates held together by the polymer.

In order that the compositions of the invention, particularly those containing amino acids or proteinaceous materials, may be adequately protected, it is necessary to insure that treatment of the particles results in at least the surface portion of each particle being continuously coated or encapsulated as completely as possible with the polymer. Pinholes or other discontinuities in the coating may allow attack on the material by rumen microflora. The use of fairly thick coatings or multiple coating techniques is thus advisable but, on the other hand, excessively thick coatings are generally to be avoided both for economic reasons and because of possible inhibition of efficacious release in the abomasum or intestine.

Generally, for smaller particles of from about 0.1 to about 1.0 mm., coating thicknesses are usually maintained at about 0.001 inch to about 0.0015 inch (0.025 to about 0.04 mm.), which usually corresponds to weight of coating equal to from about 5 to about 80 percent by weight of the material to be coated.

In a further aspect, this invention provides a method of treating ruminant animals, which comprises administering to the animal a nutrient or therapeutic composition or supplement which comprises the combination of a nutrient or therapeutic material and the hereinbefore described polymer, said combination being of such form that the material is thereby rendered resistant to attack and breakdown within the rumen of the animal but remains susceptible to breakdown and digestion within the abomasum or small intestine of the animal. In another aspect, this invention provides a method of protecting a nutrient or therapeutic material from degradation by moisture in storage, said method comprising the combination of said nutrient or therapeutic material and said hereinbefore described polymer, said combination being resistant to penetration by moisture under usual storage conditions.

In order that the present invention in its various aspects may be more fully and completely understood, examples will now be given showing the preparation, characterization, properties and uses of typical animal feed supplements in accordance with the invention. These examples, however, are not to be construed as limiting the invention. Except where otherwise indicated all parts and percentages are by weight and temperatures are uncorrected.

EXAMPLE 1

Preparation of Imidazoline Modified Styrene-Acrylonitrile Polymer

A 500 ml. 3-necked flask equipped with a mechanical stirrer, thermowell with thermometer, a nitrogen purge inlet, and a water cooled condensor was charged with 1.0 g. of zinc sulfate heptahydrate (0.0035 mole), 100.0 g. of aminoethyl-ethanolamine (AEEA) (0.96 mole 4.8 fold excess), and 42.6 g. of a styrene-acrylonitrile resin having a molecular weight of 190,000 and containing about 0.20 mole of nitrile groups. A slow nitrogen purge was started and the reaction mixture was heated to 150° C. at which point ammonia evolution was detected as shown by the change in color of an ammonia trap from yellow to blue (bromocresol green indicator). The reaction mixture was heated to 198° to 209° C. for three hours giving a light yellow solution of polymer. A total of 84.6 cc (0.0846 mole) of 1.000 N HCl was consumed by titration of the ammonia and entrained AEEA collected in the trap.

The polymeric product was recovered by precipitating in water while stirring. Filtration gave a white solid filter cake which was washed three times with water and dried under vacuum overnight at room temperature. The product was a finely divided, white, free-flowing powder. NMR analysis of the dry polymer dissolved in $CDCl_3$ showed it contained 14.5 mole percent hydroxyethyl imidazoline functionality.

Following the above procedure various imidazoline modified polymers were prepared and tested as shown in Table I.

The imidazoline modified copolymers were tested for performance at pH 6 and 3 by studying the rate of migration of methionine through a thin diaphragm (0.006–0.009 inch) of the pH sensitive resin. Methionine is a common animal feed supplement. The thin diaphragm mimics the coating around the prills. A resin which is a barrier to the migration of the methionine through it as a diaphragm in a pH 6 buffer solution should also be a barrier at pH 6 as a coating over methionine prills. Also, a resin which swells enough at pH 3 to allow rapid migration of methionine through it as a diaphragm should also release methionine at pH 3 as a coating over methionine prills. The credibility of results with a diaphragm depends upon its thinness and its integrity during the experiment. The diaphragms were produced by first casting sheets from one gram of resin dissolved in about 9 g of chloroform and poured evenly over an area of 2¼ by 4 inches marked out upon a taut flat sheet of Tedlar (polyvinyl fluoride film) taped to a level surface (e.g., Formica board) in a hood. After about 16–20 hours of drying (overnight), the sheets were carefully removed from the Tedlar without damage and one inch diameter disks are punched out with a sharp punch. The disks were used as diaphragms in the cell used to test the performance of the resin. A plasticizer was usually included with the resin in the chloroform solution in order to reduce brittleness and increase the rate and amount of swelling at pH 3. The disks were allowed to dry for at least two days at room conditions before testing. To test a resin for performance two elbows of #15 Pyrex glass O-ring joints were clamped together with gaskets and a diaphragm to form a cell. The cell parts had been warmed to about 80° C. in an oven in order to keep the diaphragm slightly softened when the flanges of the cell are clamped. An intact disk of resin (free of pinholes or cracks) had been selected by viewing against a source of bright light. The disk had been warmed on a surface of about 70° C. (e.g., the flat metal rack in the 80° C. oven) and flattened by gentle pressing before clamping into the cell. After the cell was formed about 10 g of a pH buffer solution containing 3% of dissolved methionine was added to the left arm of the cell and 10 g of the same pH buffer without the methionine was added to the right arm of the cell. The integrity of the diaphragm was established by placing a stainless steel rod in each arm of the cell and measuring the electrical resistance across the diaphragm. When the resistance was greater than $10^7$ ohms (top of the range of the Leeds and Northup AC bridge), it was assumed that the diaphragm was intact. Without the diaphragm, the resistance of the buffer solution between the electrodes was less than $10^3$ ohms. The tops of the cell were then capped with a thin plastic film (e.g., SARAN WRAP ®) held tightly in place with small rubber bands and the cell placed on a slowly revolving rack (e.g., 2.3 RPM for these studies) in a 38°–40° C. chamber. (The body temperature of a cow is 38° C.) For the pH 6 buffer, about 24 hours of incubation was allowed to match the residence time of food in the rumen of a cow. For the pH 3 buffer, 3 hours of incubation was allowed to match the residence time of food in the abomasum and upper intestine of a cow. After the incubation period, the solutions were separately filtered and the concentration of methionine in each solution was determined by NMR spectrometry (EM 360 60 MHz NMR Spectrometer, Varian Instruments), using the area of the major peak for methionine (pendant $CH_3$ attached to S in the molecule [$CH_3SCH_2CH_2CH(NH_2)COOH$]) related to the area at a concentration of 3%. The accuracy of the determination appears to be ±0.05% methionine. The percent migration was calculated for the time period involved. The maximum migration would be 50% of the 3% methionine; or 1.5% methionine in the right arm.

Table I

Methionine Migration and Swelling Experiments with Thin Cast Resins in pH 6.3 and pH 3.2 Buffer Solutions at 40° C.

| Run | 10% Chloroforms Viscosity (cps) | Diaphragm Composition | Methionine Migration (% of 3%) pH 6.3 Hrs | % | pH 3.2 Hrs | % | Swelling Weight Gain (%) pH 6.3 Hrs | % | pH 3.2 Hrs | % |
|---|---|---|---|---|---|---|---|---|---|---|
| 1 | 45.5 | 12.8 mole % $IM^6$-S/$An^1$ + 10% $DBP^4$ | 21 | 0 | 3 | 0 | 24 | 33 | 3 | 55 |
| 2 | 35 | 14.5 mole % $IM^6$-S/$AN^1$ + 10% DBP | 21 | 7 | 3 | 15 | 21.5 | 44 | 3 | 156 |
| 3 | 27.5 | 16.1 mole % $IM^6$-S/$AN^1$ + 10% DBP | 21 | 13 | 3 | 50 | 21 | 60 | 3 | 334 |
| 4 | 18.5 | 16.7 mole % $IM^6$-S/$AN^2$ + 5% DBP | 23 | 17 | 3 | 50 | 23 | 41 | 3 | disintegrated |
| 5 | 28 | 18.2 mole % $IM^6$-S/$AN^1$ + 10% DBP | 18.5 | 15 | 3 | 50 | 18 | 62 | 3 | disintegrated |
| 6 | 95,000 | 20 mole % $IM^6$-S/$AN^1$ + 10% C.A.-$4^5$ | 23 | 10 | 3 | 14 | 24 | 52 | 3 | 459 |
| 7 | 29.5 | 21.9 mole % $IM^6$-S/$AN^3$ + 5% DBP | 24 | 32 | 3 | 50 | 24 | 99 | 3 | dissolved |
| 8 | 28 | 22.4 mole % $IM^6$-S/$AN^1$(no plasticizer) | 23.5 | 20 | 3 | 50 | 23.5 | 67 | 3 | disintegrated |
| 9 | 28 | 22.4 mole % $IM^6$-S/$an^1$ + 10% DBP | 18 | 17 | 1 | 50 | 17 | 84 | 1 | disintegrated |
| 10 | 26.5 | 25 mole % $IM^6$-S/$an^1$ + 5% DBP | 25 | 50 | 1 | 50 | 25 | 141 | 1 | disintegrated |

Footnotes to Table I
[1] Polymer containing about 75 weight percent polymerized styrene and 25 weight percent polymerized acrylonitrile and having a molecular weight of about 185,000.
[2] Same as [1] except MW about 65,000
[3] Polymer containing about 65 weight percent polymerized styrene and 35 weight percent polymerized acrylonitrile and having a molecular weight of about 150,000.
[4] DBP = dibutylphthalate plasticizer.
[5] C.A.-4 = Citroflex ® A-4 plasticizer.
[6] IM = Hydroxyethyl imidazoline modification.

From Table I, Run 1, it is seen that a modification of 12.8 mole % allowed no methionine migration in 3 hours at pH 3.2. Thus, this amount of modification is too low. At 25 mole % modification, Run 10, the diaphragm did not prevent migration at pH 6.3, which indicates that this modification is too high. The preferred amount of modification appears to be about 16 mole %, Run 3.

Various modifications may be made in the present invention without departing from the spirit or scope thereof and it is understood that we limit ourselves only as defined in the appended claims.

What is claimed is:

1. A nutrient or therapeutic orally administered composition for ruminant animals comprising the composition of a nutrient or therapeutic material and coated thereon an hydroxyethyl imidazoline modified styrene-acrylonitrile polymer composition containing from about 15 to about 35 weight percent polymerized acrylonitrile, from about 85 to about 65 weight percent styrene, having a molecular weight of from about 60,000 to about 200,000, which polymer contains from 14 to 23 mole percent hydroxyethyl imidazoline modification, said combination being of such form that the material is thereby rendered resistant to attack and breakdown within the rumen of the animal but remains susceptible to breakdown and digestion within the abomasum or small intestine of the animal.

2. A composition as in claim 1, wherein the nutrient or therapeutic material is in the form of discrete bodies or particles having a substantially continuous surface coating of said polymer.

3. A composition as in claim 1, wherein the particles of the nutrient or therapeutic material are dispersed throughout a matrix of said polymer.

4. A composition as in claim 1, wherein said nutrient material is an amino acid.

5. A composition as in claim 4, wherein said amino acid is methionine.

6. A composition as in claim 1, wherein said therapeutic material is an antibotic.

7. A composition as in claim 1, wherein said therapeutic material is an anthelmintic.

8. A method for treating ruminant animals comprising orally administering to the animal a nutrient or therapeutic composition or supplement comprising a combination of a nutrient or a therapeutic material having coated thereon an hydroxyethyl imidazoline modified styrene-acrylonitrile polymer composition containing from about 15 to about 35 weight percent polymerized acrylonitrile, from about 85 to about 65 weight percent styrene, having a molecular weight of from about 60,000 to about 200,000, which polymer contains from 14 to 23 mole percent hydroxyethyl imidazoline modification, the coated product thereby rendered resistant to attack and breakdown within the rumen of the animal while susceptible to breakdown and digestion within the abomasum or small intestine of the animal.

9. A method as in claim 8, wherein the nutrient or therapeutic material is in the form of discrete bodies or particles having a substantially continuous surface coating of said polymer.

10. A method as in claim 8, wherein particles of the nutrient or therapeutic material are dispersed throughout a matrix of said polymer.

11. A method as in claim 8, wherein said nutrient material is an amino acid.

12. A method as in claim 11, wherein said amino acid is methionine.

13. A method as in claim 8, wherein said therapeutic material is an antibotic.

14. A method as in claim 8, wherein said therapeutic material is an anthelmintic.

* * * * *